United States Patent [19]

Feldt

[11] 4,095,459
[45] Jun. 20, 1978

[54] APPARATUS FOR DETERMINING MOISTURE CONTENT

[76] Inventor: Anthony L. Feldt, Park, Kans.

[21] Appl. No.: 721,314

[22] Filed: Sep. 7, 1976

[51] Int. Cl.$^2$ .............................................. G01N 5/04
[52] U.S. Cl. ....................................... 73/76; 100/110
[58] Field of Search .............. 73/73, 76, 94; 100/104, 100/110, , 125, 126, 127

[56] References Cited

U.S. PATENT DOCUMENTS

| | | | |
|---|---|---|---|
| 2,551,886 | 5/1951 | Jones | 100/125 |
| 2,907,203 | 10/1959 | Langmead | 73/94 X |
| 3,890,830 | 6/1975 | Dyck | 73/94 |
| 3,979,947 | 9/1976 | Parkinson | 73/73 |

Primary Examiner—Charles A. Ruehl
Attorney, Agent, or Firm—Sheridan, Ross, Fields & McIntosh

[57] ABSTRACT

Apparatus for use in determining the moisture content of fodder, more particularly ensilage, by subjecting a given weight of ensilage to a predetermined pressure to force moisture from the ensilage. The apparatus includes a hollow cylinder which is removably supported on a bottom plate, which plate is in turn removably mounted on a base. A plurality of small diameter openings are formed in the walls of the cylinder and through the hollow plate. These openings provide passages through which liquid forced out of the fodder can escape from the cylinder. A piston which is free to move within the hollow cylinder is operatively connected to a source of power to apply pressure to the ensilage placed in the cylinder between the piston and the bottom plate. Once all the liquid that can be squeezed out of the ensilage by the application of a given force has in fact been squeezed out, removal of the bottom plate and the application of a small force on the piston will drive out the plug of remaining ensilage through an opening in the base substantially equal in diameter to that of the cylinder so that plug can be weighed to determine the amount of liquid forced from it.

9 Claims, 5 Drawing Figures

U.S. Patent  June 20, 1978  Sheet 1 of 2  4,095,459
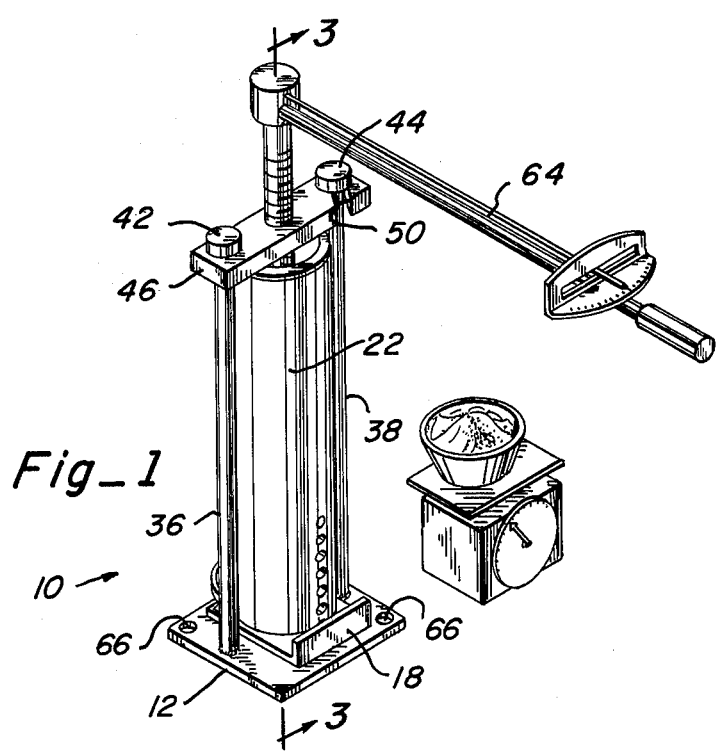
Fig_1
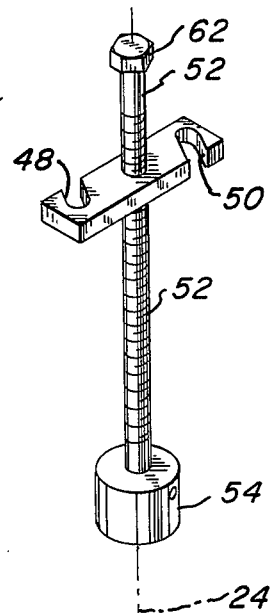
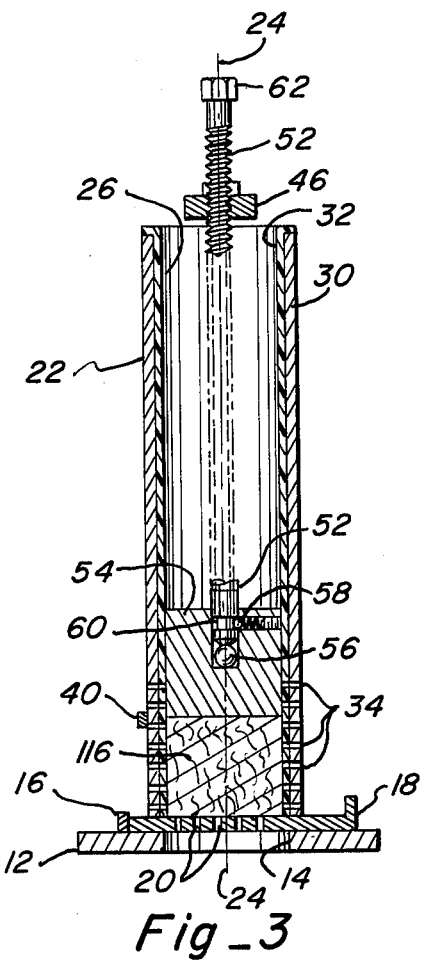
Fig_3
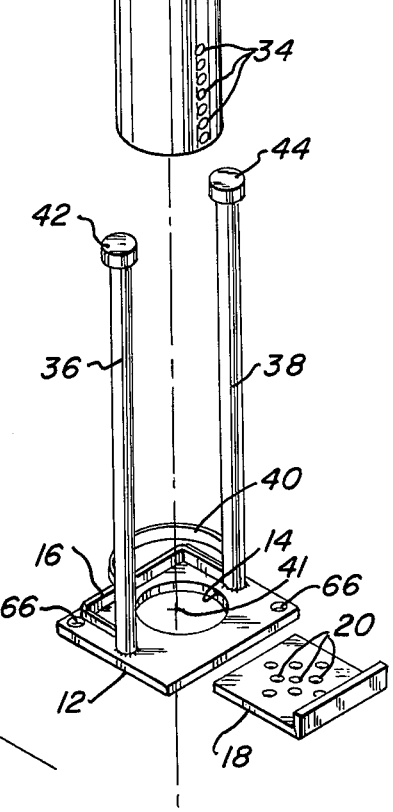
Fig_2

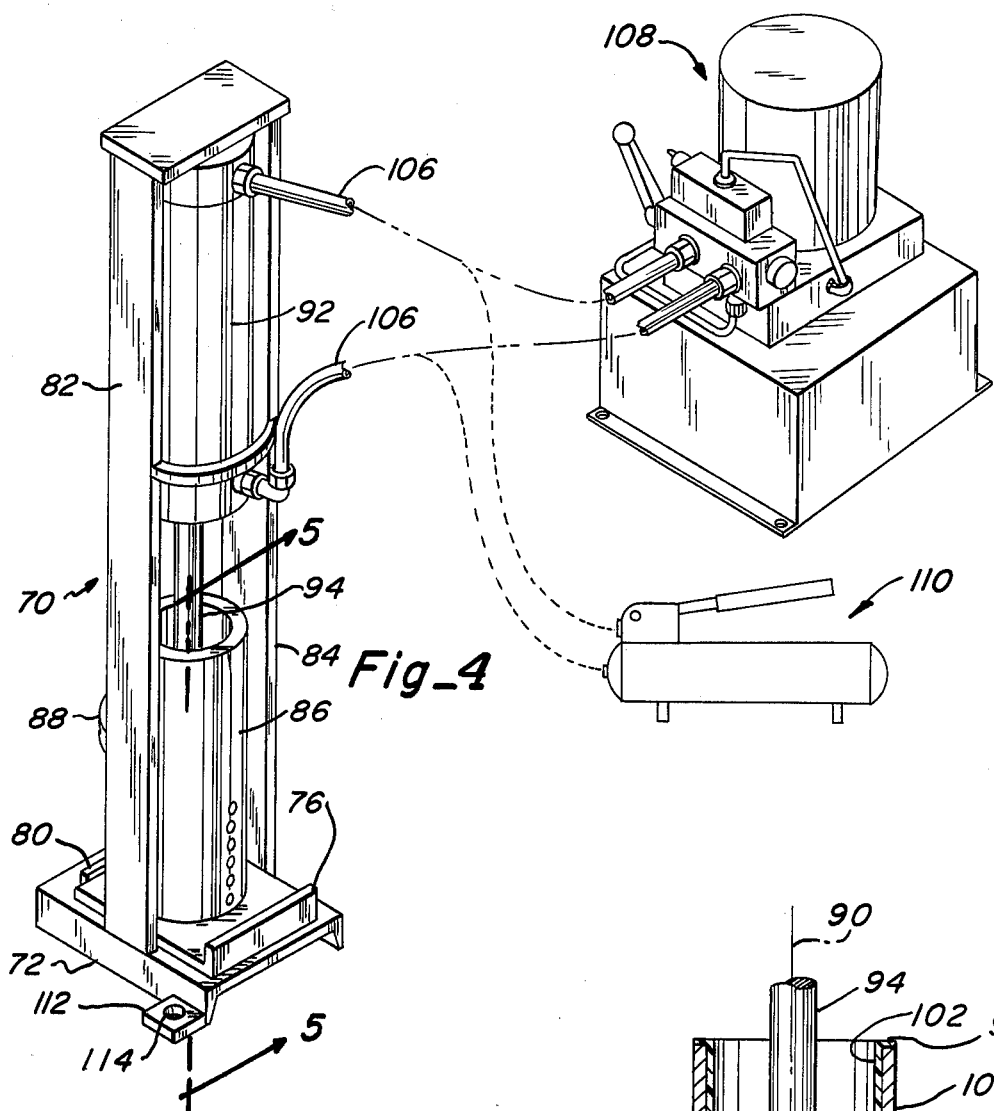
Fig_4
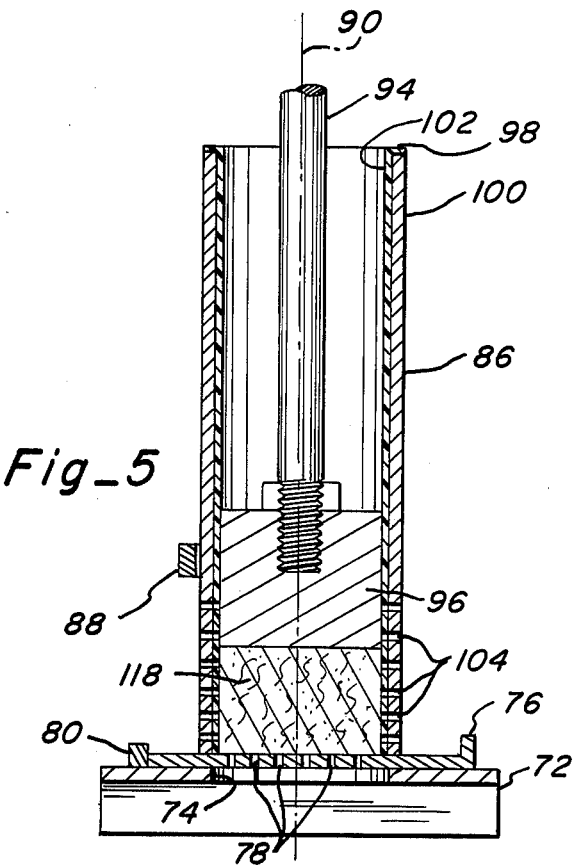
Fig_5

APPARATUS FOR DETERMINING MOISTURE CONTENT

BACKGROUND OF THE INVENTION

1. Field of the Invention

This invention is in the field of devices for applying a predetermined pressure to a given weight of material placed in the device to squeeze out a portion of the liquid content of the material and for facilitating the removal of the remaining material in the device so that the weight of the remaining material can be readily and accurately determined.

2. Description of the Prior Art

Ensilage is a succulent feed for livestock, particularly cattle which has nearly as much food value as fresh feed. Green grains and grasses such as corn, wheat, sorghum to be converted into ensilage are chopped into small pieces and stored in a silo. Because it is such a good food for cattle, it obviously has economic value, and thus is bought and sold. However, since ensilage is made from green plants, the moisture content of ensilage can and does vary widely. Thus, there is a need for a reliable apparatus to be used in determining moisture content of ensilage which is readily portable so that it can be taken where the ensilage is stored and which permits the desired measurements to be obtained quickly. It is also essential that the measurements be to an acceptable degree of accuracy. The power needed by the apparatus should be such that it can be provided from typical power sources that are readily available at silos. In the absence of any such power sources, the power required should be such that one person can easily provide it.

The prior art teaches weighing a sample to be tested, drying the sample until the moisture in it is substantially entirely removed and then reweighing the sample to calculate the original amount of moisture in the sample in terms of either its original or its dry weight. The prior art also teaches the use of electrically heated ovens to remove substantially all the moisture from a sample or of using microwave energy to dry out the moisture from a sample.

The prior art has also taught the application of a predetermined amount of pressure to a given quantity of vegetables, particularly peas, draining from the compressed vegetables moisture liberated by the pressure, and collecting the moisture squeezed out of the vegetables. The amount of moisture is used as an indication of the grade or quality of the vegetables after they are canned. The prior art apparatus referred to above is laboratory type equipment to which the samples are brought and thus does not meet the need for apparatus that is readily portable so that it can be taken to the material to be measured, that can operate without substantial quantities of electrical energy, and that can be used to measure quickly and with a sufficient degree of accuracy the moisture content of a sample of ensilage.

SUMMARY OF THE INVENTION

The present invention provides apparatus which can be used to apply pressure to a sample of a given weight of ensilage to remove moisture from the sample and which readily permits the complete removal of substantially all of the remaining portion of the sample from the apparatus. The apparatus of the present invention includes a base, a bottom plate which is removably mounted on the base and a hollow cylinder removably mounted on the bottom plate. A piston is positioned in the cylinder and openings are provided through the walls of the cylinder and through the bottom plate through which moisture forced out of the sample can escape. The balance of the sample after the moisture has been removed from it and after the bottom plate is removed is forced through an opening in the base substantially equal in diameter to the diameter of the hollow cylinder. The force applied to the piston can be produced by applying torque to a threaded piston rod threaded through an upper plate which upper plate is attached to the base, or by a hydraulic cylinder which is attached to the base. The movable element or piston of the hydraulic cylinder is connected to the piston of the apparatus.

It is therefore an object of the invention to provide improved portable apparatus which can be used in determining the moisture content of fodder.

It is another object of this invention to provide improved apparatus for determining the moisture content of ensilage which is portable, quick in operation and requires no special or large power supply.

It is still another object of this invention to provide improved apparatus for determining the moisture content of ensilage in which the recovery of the balance of the sample of ensilage which has been subjected to a predetermined pressure to squeeze out moisture from the sample is easily accomplished.

BRIEF DESCRIPTION OF THE DRAWINGS

Other objects, features and advantages of the invention will be readily apparent from the following description of certain preferred embodiments, taken in conjunction with the accompanying drawings, although variations and modifications may be effected without departing from the spirit and scope of the novel concepts of the disclosure and in which:

FIG. 1 is an isometric view of an embodiment of the present invention illustrating the various features thereof;

FIG. 2 is an exploded view of the apparatus of FIG. 1;

FIG. 3 is an enlarged sectional view taken on lines 3—3 of FIG. 1;

FIG. 4 is an isometric view of a second embodiment of the present invention; and FIG. 5 is an enlarged partial section taken on lines 5—5 of FIG. 4.

DESCRIPTION OF THE PREFERRED EMBODIMENT

The apparatus, or press, 10 illustrated in FIGS. 1 through 3, is provided with a base 12. A circular opening 14 is formed through base 12 as is best seen in FIGS. 2 and 3. Stop, or vertical wall, 16 is formed on the top surface of base 12 to position bottom plate 18 so that a plurality of openings 20 which are formed through bottom plate 18 are in communication with the space within opening 14 when bottom plate 18 is positioned on base 12 and in contact with stop 16. Hollow cylinder 22 has a longitudinal axis 24. The diameter of the cylindrical opening 26 of cylinder 22 is substantially constant. The walls 28 of cylinder 22 are made from two concentric layers of material. Outer layer 30 is made of a suitable metal such as steel, and inner layer 32 is formed of a suitable plastic material such as nylon, Teflon, or the like. A plurality of openings 34 are formed through the lower portion of the walls 28 of cylinder 22.

Metal tie rods, or bars, 36, 38 are permanently secured to base 12, by welding in a preferred example, and extend substantially vertically from the top surface of base 12. A metallic rim 40 having a radius of curvature substantially equal to that of the outer surface of wall 30 of cylinder 22, is attached between tie rods 36 and 38 to position cylinder 22 so that when the bottom surface of cylinder 22 is placed in contact with bottom plate 18, the center 41 of opening 14 in base 12 will lie substantially on the longitudinal axis 24 of cylinder 22.

Each of the tie rods 36, 38 is provided with an enlarged head 42, 44. Upper plate 46 is provided with a pair of slots 48, 50 within which tie rods 36, 38 can fit. When upper plate 46 is positioned so that tie rods 36, 38 are within slots 48, 50, as illustrated in FIG. 1, then the upper surface of plate 46 can contact the heads 42, 44. Upper plate 46 is also provided with an opening provided with threads through which shaft 52 is threaded. Piston 54 is rotatably attached at the lower end of shaft 52 so that while shaft 52 is turning in the threaded opening in upper plate 46 to apply force to piston 54, piston 54 need not rotate. Referring to FIG. 3, ball bearing 56 is positioned between the bottom end of shaft 52 and piston 54 to transmit forces directed toward base 12 from shaft 52 to piston 54. Ball bearing 58 is mounted in piston 54 so that it engages a circumferential groove 60 in shaft 52 and thus transmits forces from shaft 52 to piston 54 directed away from base 12. A hexagonal head 62 is formed on the top of shaft 52 so that a predetermined magnitude of torque can be applied to shaft 52 by a conventional torque wrench 64. Openings 66 in base 12 are provided to facilitate removably securing press 10 to a frame or bench, for example, if desired.

In FIGS. 4 and 5 a second embodiment of the invention is illustrated. Apparatus, or hydraulic press, 70 has a base 72 with a circular opening 74 formed through it. A bottom plate 76 which is provided with a plurality of openings 78 is adapted to be positioned on the upper surface of base 72 by stop 80 so that openings 78 are in communication with opening 74. Two support bars or rods 82, 84 are also secured to the top surface of base 72 and assist in positioning bottom plate 76 on base 72. Hollow cylinder 86, which is substantially identical in construction to cylinder 22 is removably mounted on bottom plate 76. Metallic positioning means, or rim, 88 is attached to bars 82, 84 to position cylinder 86 so that the center of opening 74 lies on the longitudinal axis 90 of cylinder 86. A conventional hydraulic cylinder 92 having a piston rod 94 is attached to bars 82, 84 so that the longitudinal axis of rod 94 substantially coincides with the longitudinal axis 90 of cylinder 86. Piston 96 is attached to piston rod 94 by being threaded to it, for example, and is constrained to move within cylinder 86 in directions parallel to longitudinal axis 90 of cylinder 86. The walls 98 of cylinder 86 are made of two concentric layers of material. Outer layer 100 is preferably made of steel and inner layer 102 is made of a plastic material such as nylon or teflon. A plurality of openings 104 are formed through the lower portion of the walls 98 of cylinder 86.

Hydraulic lines 106 provide hydraulic fluid under pressure to hydraulic cylinder 92 to apply force to piston rod 94 to cause piston 96 to move both toward and away from the base 72 of press 70. Hydraulic fluid under pressure can be supplied by a conventional electrically powered pump 108 which is provided with appropriate controls, by the hydraulic pump of a tractor which is not illustrated, or by hand pump 110. Base 72 is provided with a pair of lugs 112 at opposite corners of base 72 which are designed to facilitate removably securing press 70 to any suitable frame by bolts, for example, that will fit through openings 114 in lugs 112.

In operation of the embodiment illustrated in FIGS. 1, 2 and 3 a given weight of ensilage, 100 grams for example, is placed in cylinder 22. Base 12 is placed preferably on a flat surface or is removably secured to a suitable frame, which is not illustrated, to prevent its turning about axis 24. Bottom plate 18 is positioned by stop 16 and rods 36, 38 on base 12 so that openings 20 are in communication with opening 14. Cylinder 22 may then be placed on bottom plate 18 in contact with rim 40. Alternatively, the sample of ensilage 116 can be inserted into cylinder 22 after cylinder 22 is positioned on bottom plate 18. Shaft 52 is threaded into the threaded opening in upper plate 46 and piston 54 which is rotatably connected to shaft 52 is inserted into the upper portion of cylinder 22. Upper plate 46 is positioned so that the tie rods 36, 38 fit within slots 48, 50 of upper plate 46 and the top surface of plate 46 is in a position to enagage the heads 42, 44 of tie rods 36, 38. Shaft 52 is then rotated by torque wrench 64 which uses a socket that fits hexagonal head 62 of shaft 52 to apply torque to shaft 52. As shaft 52 rotates with respect to upper plate 46, shaft 52 exerts a force on piston 54 directed toward base 12. Shaft 52 is rotated until a predetermined torque, in the range of from 100 to 120 foot pounds, in a preferred embodiment, is applied to shaft 52 by wrench 64. As is well know, the torque applied to shaft 52 is multiplied by the mechanical advantage of the threaded shaft to apply a predetermined force to piston 54. Piston 54 applies pressure to the mass 116 of ensilage between piston 54 and bottom plate 18, the magnitude of which is a function of the force applied to piston 54 and the area of piston 54 in contact with ensilage 116. As a result of this pressure, moisture in sample 116 is forced out through the openings 34 in cylinder 22 and through the openings 20 in bottom plate 18. Once the desired magnitude of torque has been applied to shaft 52 and all the moisture has escaped that will escape from sample 116 at that particular torque and corresponding pressure, wrench 64 is used to turn shaft 52 to relieve the pressure transmitted through ensilage 116 to bottom plate 18. Once this pressure is sufficiently removed bottom plate 18 is removed. To force out the plug of ensilage 116 remaining, wrench 64 can again be turned to force out plug 116 from cylinder 22 through the opening 14 in base 12 so that substantially all of plug 116 can be collected for weighing. Plug 116 is then weighed and the amount of weight lost substantially equals the moisture that was forced from the sample during the test.

In the embodiment of the invention illustrated in FIGS. 4 and 5, the operation of the press 70 is similar to that of press 10 except that the force exerted on piston 96 is from a hydraulic cylinder 92 rather than from a screw press. In this embodiment the force applied to the piston 96 and thus to the sample of ensilage 118 is a function of the pressure of the hydraulic fluid in hydraulic cylinder 92 multiplied by the cross-sectional area of the piston of hydraulic cylinder 92. However, whether the source is hydraulic pressure or torque multiplied by the mechanical advantage of a threaded shaft turning in a threaded bolt, a predetermined pressure in the range from 1000 to 2000 pounds per square inch is applied against the sample to be tested. Tests support the conclusion that pressures in this range provide very satisfactory results in determining the moisture content of ensilage.

In running tests using the embodiment of the invention illustrated in FIGS. 4 and 5, base 72 of press 70 may be attached to an object such as a wooden frame which has some means for fastening base 72 to it so that it is not apt to fall or be knocked over. This can be accomplished by inserting bolts through openings 114 in lugs 112 to secure base 72 to such an object preferably in substantially an upright position. Movable plate 76 is placed in position on base 72, the ensilage to be tested is weighed and the proper amount, 100 grams for example, is placed inside of cylinder 86. Cylinder 86 is placed on plate 76 in contact with rim 88 so that axis 90 substantially coincides with the longitudinal axis piston rod 94. Hydraulic pressure is then applied to cylinder 92 from hand pump 110, for example, to drive piston rod 94 downwardly so that the piston 96 will exert pressure on the mass of ensilage 118 between piston 96 and bottom plate 76. The magnitude of the pressure is predetermined and is sufficient to squeeze moisture in sample 118 out through openings 104 in cylinder 86 and through the openings 78 in bottom plate 76. When the desired pressure in the range of from 1000 to 2000 pounds per square inch has been applied to the mass of ensilage 118 and after moisture ceases to flow out of the mass of ensilage 118, a matter of only a few seconds after the predetermined maximum pressure has been reached, the controls on the source of hydraulic pressure can be changed to no longer apply force to piston 96. Once piston 96 is no longer applying pressure in mass 118, bottom plate 76 can be removed. Then a slight amount of hydraulic pressure can be applied to cylinder 92 to force the plug of remaining ensilage 118 from cylinder 86 through opening 74 in base 72.

Hydraulic cylinders have the advantage that if electrical power is available where the tests are desired to be run, then an electrically powered source of hydraulic pressure 108 can be used to provide the hydraulic fluid under pressure through lines 106 to hydraulic cylinder 92. Since some tractors are fitted with hydraulic pumps, a tractor also could be the source of the pressurized hydraulic fluid for cylinder 92.

The plastic linings 32, 102 of cylinders 22, 86 reduce the frictional losses between the pistons 54, 96 and cylinders 22, 86 encountered in compressing ensilage and they also have the advantage that substantially all of the plugs of compressed ensilage remaining after the excess moisture has been squeezed from them can be removed through the openings 14, 74 formed in the bases 12, 72 of the two embodiments of the invention since the ensilage does not adhere strongly to the plastic inner linings of cylinders 22, 86. Because of the fibrous nature of ensilage, a substantial amount of pressure can be applied to the mass to be tested without causing an excessive amount of solid material to be forced through the openings 34, 104, in the cylinders 22, 86 and through the openings 20, 78 of the bottom plates 18, 76.

From the foregoing it is clear that the apparatus of my invention can be used to determine the moisture content of fodder and more particularly ensilage by subjecting a sample of a given weight to a predetermined pressure to squeeze out moisture from the sample and then to facilitate the removal of the remainder of the sample for weighing. As a result it is possible to determine the amount of moisture that was removed. Since there is a correlation between the dry weight of the sample and the weight of the sample after it has been subjected to a predetermined pressure, it is possible to estimate, or calculate, the amount of dry material in a sample to an acceptable degree of accuracy.

The apparatus of my invention by being portable in the sense that is can be carried long distances in a car or pickup truck and by not requiring large quatities of power, i.e. its power requirements are capable of being provided by an individual, can be used at any location where ensilage is found. Further, the apparatus of my invention takes only a few minutes, at the most, to obtain measurements of the moisture content of a sample.

It should be obvious that various modifications can be made to the embodiments of my invention as disclosed herein without departing from the scope of the present invention.

What is claimed is:

1. Apparatus for subjecting a mass of moist fibrous material to a predetermined pressure comprising:
   a base,
   means forming a circular opening through the base, said opening having a center, a hollow cylinder, having a longitudinal axis, the diameter of the opening in the cylinder being substantially equal to the diameter of the circular opening through the base,
   a bottom plate,
   means forming a plurality of openings through said plate,
   means for removably mounting said bottom plate on said base so that at least some of the openings through said bottom plate communicate with the opening in said base,
   means for removably mounting said cylinder on the bottom plate so that the center of the opening in the base substantially lies on the axis of the cylinder,
   a piston adapted to move within said cylinder, and
   means for applying a predetermined force to said piston.

2. Apparatus as defined in claim 1 in which the means for applying a predetermined force to said piston includes a hydraulic cylinder operatively connected to the base and adapted to be connected to a source of pressurized hydraulic fluid.

3. Apparatus as defined in claim 1 in which the means for applying a predetermined force to said piston includes a threaded shaft adapted to be rotated in a threaded opening in an upper plate, said plate being operatively connected to the base.

4. A press for subjecting a predetermined mass of ensilage to a predetermined pressure to force moisture from the mass of ensilage, comprising:
   a base,
   means forming an opening through said base,
   guide means on said base,
   a bottom plate,
   means forming a plurality of openings through the bottom plate,
   a pair of bars fixedly mounted on said base, said guide means and said bars positioning the bottom plate so that it covers the opening through the base, and so that the openings through the bottom plate are in communication with the opening through the base,
   a hollow cylinder having walls,
   means forming a plurality of openings through the walls of the cylinder,
   a rim fixedly mounted to said base for removably positioning the hollow cylinder on the bottom plate with the interior of the cylinder in communication with the opening through the base and the openings in the bottom plate, a piston within the hollow cylinder for movement therein, and means attached to the base for applying a predetermined force to said piston, whereby ensilage placed in the cylinder between the piston and the bottom plate is subjected to a predetermined pressure.

5. A press as defined in claim 4 in which the means for applying a predetermined force to the piston is a hydraulic cylinder having a piston rod, said piston rod being attached to said piston, said hydraulic cylinder adapted to be connected to a source of hydraulic pressure.

6. A press as defined in claim 4 in which the means for applying a predetermined force to the piston comprises a threaded shaft, an upper plate, means for removably connecting the upper plate to said bars, a threaded opening formed in said upper plate, said shaft being threaded into the threaded opening in the upper plate, the piston being rotatably connected to one end of the shaft, and the other end of the shaft adapted to be rotated by a torque wrench.

7. Apparatus for subjecting a mass of moist fibrous material to a predetermined pressure comprising:

a base, means forming a circular opening through the base, said opening having a center and a diameter, wall means defining a hollow cylinder, said cylinder having a longitudinal axis and an inner diameter, said wall means being comprised of an inner and an outer layer, the inner layer being made of a plastic material, and the outer layer being made out of metal, means forming a plurality of openings through said wall means, a bottom plate, means forming a plurality of openings through said plate, bar means fixedly attached to the base, stop means fixedly attached to said base, said bottom plate being positioned by the bar means and stop means on the base so that at least some of the openings through the bottom plate communicate with the circular opening in the base, positioning means attached to the bar means, the wall means defining a hollow cylinder being removably positioned on the bottom plate by the positioning means so that the center of the opening in the base substantially lies on the longitudinal axis of the cylinder, a piston adapted to move in the cylinder in directions substantially parallel to the longitudinal axis of the cylinder, a hydraulic cylinder attached to the bar means, said cylinder having a piston rod having a longitudinal axis, said hydraulic cylinder adapted to be connected to the source of pressurized hydraulic fluid, said hydraulic cylinder being attached to the bar means so that the longitudinal axis of the piston rod substantially coincides with the longitudinal axis of the cylinder, said piston rod being attached to the piston to cause reciprocal movement of the piston within the wall means defining a hollow cylinder.

8. The apparatus as defined in claim 7 in which the diameter of the circular opening through the base and the inner diameter of the wall means defining a hollow cylinder are substantially equal.

9. A press for subjecting a predetermined mass of ensilage to a predetermined pressure to force moisture from the mass of ensilage, comprising:

a base, means forming a circular opening through the base, said opening having a center, and a diameter, a bottom plate, means forming a plurality of openings through the bottom plate, a pair of tie rods fixedly secured to the base, said rods each having an enlarged head, stop means fixedly secured to the base, the bottom plate being removably positioned on the base by the tie rods and the stop means so that the bottom plate covers the opening in the base and so that some of the openings in the bottom plate provide communication with the opening in the base, a rim fixedly secured to the rods, a hollow cylinder having an inner and an outer wall, the inner wall being of a plastic material and the outer wall being made of metal, means forming openings through the walls of the cylinder, said cylinder having a longitudinal axis and the hollow interior of the cylinder having a diameter substantially equal to the diameter of the circular opening in the base, the cylinder being in contact with the bottom plate and positioned by the rim so that the center of the circular opening in the base substantially lies on the longitudinal axis of the cylinder, a piston adapted to move within the hollow cylinder parallel to the longitudinal axis of the cylinder, an upper plate having a pair of slots on opposite sides thereof in which the tie rods are adapted to fit, a threaded opening in the top plate, a threaded shaft, said shaft being threaded through the threaded opening in the upper plate, one end of the shaft being rotatably attached to the piston and the other end adapted to be turned by a torque wrench, the upper plate being positioned so that the tie rods are in the slots in the upper plate, the upper plate contacts the enlarged heads of the tie rods, and the piston is in the hollow cylinder.

* * * * *